United States Patent [19]

Carlson et al.

[11] 4,319,966
[45] Mar. 16, 1982

[54] TECHNIQUE FOR MONITORING $SO_3$, $H_2SO_4$ IN EXHAUST GASES CONTAINING $SO_2$

[75] Inventors: Gerald L. Carlson; William M. Hickam, both of Pittsburgh, Pa.

[73] Assignee: Westinghouse Electric Corp., Pittsburgh, Pa.

[21] Appl. No.: 197,368

[22] Filed: Oct. 15, 1980

[51] Int. Cl.³ .................... G01N 27/56; G01N 27/58
[52] U.S. Cl. .............................. 204/1 T; 204/195 S
[58] Field of Search ............... 204/1 T, 195 R, 195 S, 204/1 S; 429/16, 46

[56] References Cited

U.S. PATENT DOCUMENTS

| | | | |
|---|---|---|---|
| 3,466,197 | 9/1969 | Bawa | 429/16 |
| 3,928,161 | 12/1975 | McIntyre et al. | 204/195 S |
| 4,013,412 | 3/1977 | Mukae | 204/1 T X |
| 4,042,464 | 8/1977 | Blurton et al. | 204/1 T |
| 4,154,664 | 5/1979 | Renevot | 204/1 T X |
| 4,171,253 | 10/1979 | Nolan et al. | 204/1 T X |

Primary Examiner—Arthur C. Prescott
Attorney, Agent, or Firm—M. P. Lynch

[57] ABSTRACT

The $SO_3$, $H_2SO_4$ content of a gas environment containing $SO_2$ and $H_2O$ is measured by cooling the gas to a temperature to convert $SO_3$ in the presence of $H_2O$ to $H_2SO_4$ to effectively separate $SO_3$, $H_2SO_4$ from $SO_2$ to permit the individual measurements of $SO_x(SO_2+SO_3)$, $SO_2$ and $SO_3$, $H_2SO_4$.

7 Claims, 10 Drawing Figures

TECHNIQUE FOR MONITORING SO₃, H₂SO₄ IN EXHAUST GASES CONTAINING SO₂

BACKGROUND OF THE INVENTION

Solid electrolyte detectors for the on-line monitoring of sulfur-bearing pollutants $SO_2$, $SO_3$, i.e. $SO_x$, have recently been developed and are described in detail in the issued Canadian Pat. No. 1,040,264, entitled "Solid State Sensor For Anhydrides", issued Oct. 10, 1978, which is assigned to the assignee of the present invention and incorporated herein by reference. This inventive concept is the subject matter of pending U.S. Patent application Ser. No. 718,511 now U.S. Pat. No. 4,282,078. The operation of the $SO_x$ detector described in the above-referenced patent and patent application is based on potentiometric measurements across a solid electrolyte element of potassium sulfate ($K_2SO_4$), wherein accurate measurements of sulfur-bearing pollutants over a concentration range of 0.1 parts per million to 10,000 parts per million can be realized. The sensor thus described is uniquely sensitive to $SO_x$. The presence of other common pollutants such as $CO_2$, $CH_4$ and $NO_x$ does not interfere with the $SO_x$ measurements.

SUMMARY OF THE INVENTION

The disclosed technique utilizes the condensation property of $SO_3$ as $H_2SO_4$ (liquid) and uses this to quantitatively separate $SO_3$ and $H_2SO_4$ from $SO_2$ by appropriate temperature control. In accordance with the disclosed technique, the above-referenced solid electrolyte electrochemical cell detector can be made to respond to total $SO_x$, or separately to $SO_2$ or $SO_3$, $H_2SO_4$.

BRIEF DESCRIPTION OF THE DRAWINGS

The invention will become more readily apparent from the following exemplary description in connection with the accompanying drawings.

DESCRIPTION OF THE PREFERRED EMBODIMENT

The $SO_x$ solid electrolyte electrochemical cell sensor described in the above-referenced patent and patent application, and employed herein, consists of a solid electrolyte member having electrodes disposed on opposite surfaces thereof wherein the electrodes are typically platinum. The cell can be represented as follows:

$$SO_3(P_1), O_2(P_1') \; Pt/K_2SO_4/Pt, \; O_2(P_2'), SO_3(P_2)$$

wherein the electrode reactions correspond to:

$$SO_3 + \tfrac{1}{2}O_2 + 2e^- \rightleftharpoons SO_4^=$$

The EMF of this solid electrolyte electrochemical concentration cell is defined by the Nerst equation:

$$E = \frac{RT}{2F} \ln \frac{P_1 SO_3 \times (P_1'O_2)^{\frac{1}{2}}}{P_2 SO_3 \times (P_2'O_2)^{\frac{1}{2}}}$$

where:
E = EMF;
R = gas constant;
T = temperature (°K.); and
F = Faraday.

Figure 1:
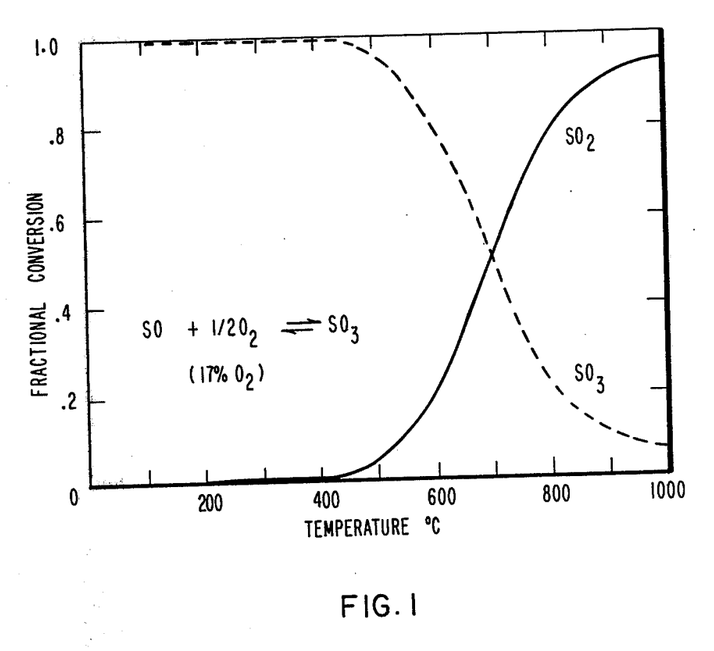
FIG. 1 is a graphical illustration of the conversion of $SO_2$ to $SO_3$.

Due to the following equilibrium relationship $$SO_3 \rightleftharpoons SO_2 + \tfrac{1}{2}O_2$$

the cell will respond to either $SO_2$ or $SO_3$ and the species involved in the cell reaction will depend on the temperature of the cell. The temperature dependence of the $SO_2$–$SO_3$ equilibrium is shown in FIG. 1. The equilibrium in the vicinity of the platinum electrode, considering platinum to be catalytic, is reached very rapidly.

The operation of the cell in accordance with the Nernst equation requires the establishment of a stable $SO_x$ reference at a reference electrode of the cell such that at a given cell temperature the change in EMF produced by the cell is a function of the $SO_x$ of the monitored gas mixture at the opposite, or sensing, electrode. A change in the EMF is indicative of a change in the partial pressure of $SO_x$ at the sensing electrode. The Nernst equation for monitoring the partial pressure of $SO_2$ in a monitored gas mixture present at the sensing electrode of the cell is represented as follows:

$$E = \frac{RT}{2F} \ln \frac{pSO_2 \times pO_2}{pSO_2' \times pO_2'}$$

The operating temperature for the cell is typically between 600° and 1000° C.

In accordance with the above mode of operation of the previously disclosed $SO_x$ responsive solid electrolyte cell it is not possible to discriminate between $SO_3$ and $SO_2$ and in fact the measurement provided is an indication of the total $SO_x$ concentration. Furthermore, as is evident from the above representation of the Nernst equation, the oxygen content of the monitored gas must be known or the oxygen pressures $pO_2$ and $pO_2'$ maintained equal.

Figure 2:
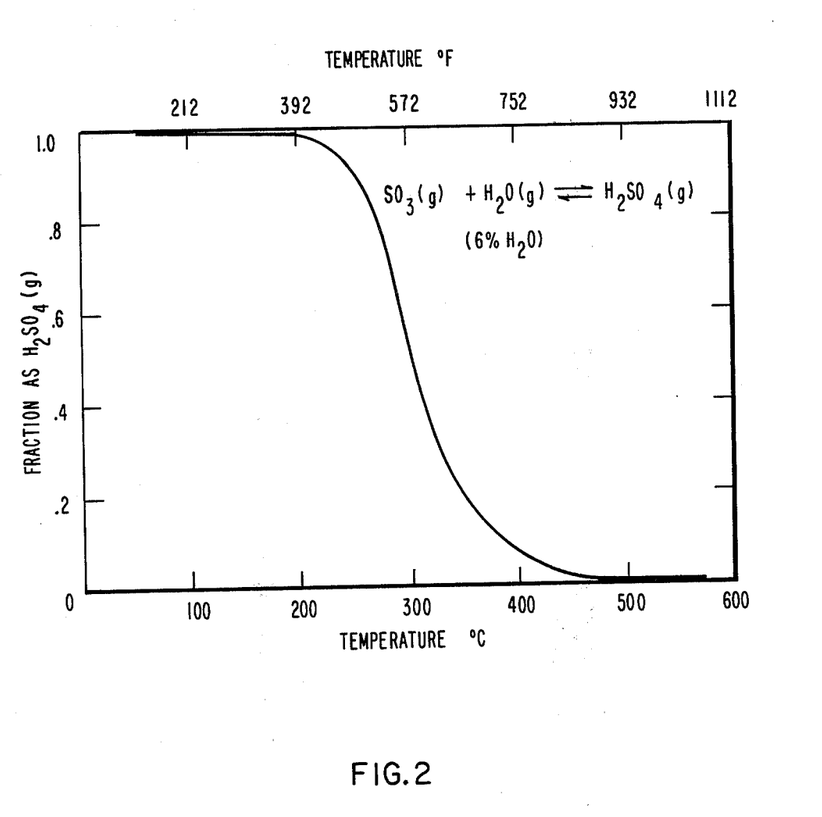
FIG. 2 is a graphical illustration of the conversion of $SO_3$ to $H_2SO_4$.

It has been determined that $SO_3$ reacts spontaneously and reversibly with water vapor to form $H_2SO_4$. The thermodynamic equilibrium for this gas phase reaction as a function of temperature is shown in FIG. 2.

Figure 3:
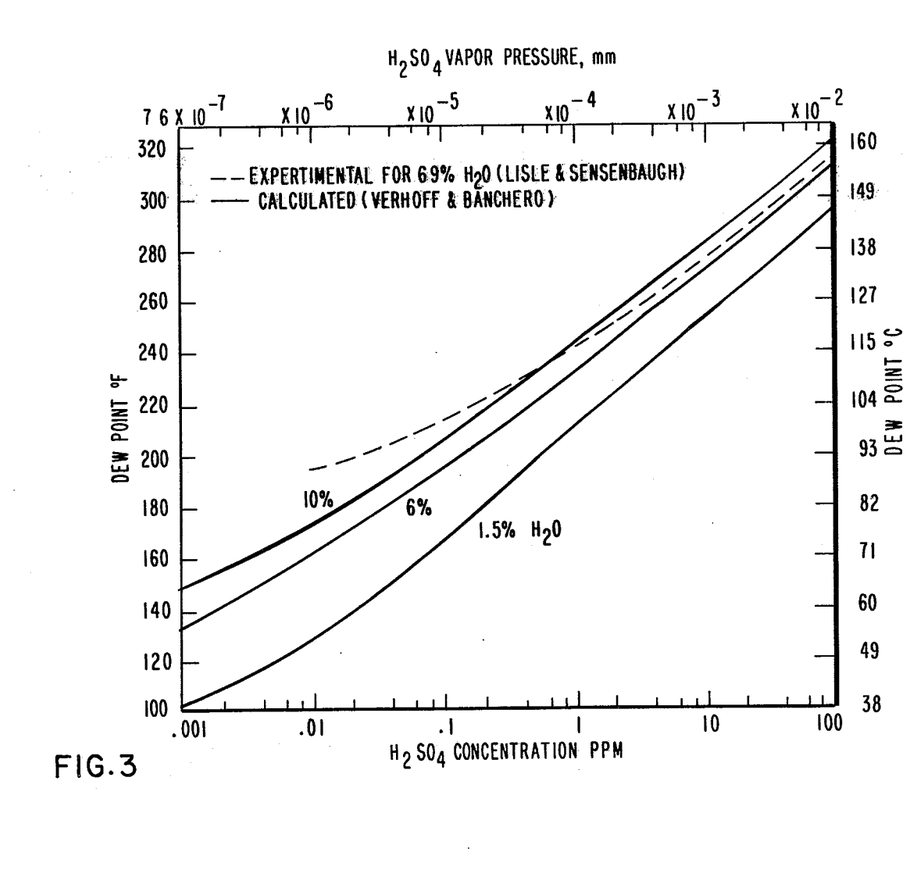
FIG. 3 is a graphical illustration of acid dew point as a function of $H_2SO_4$ concentration.
Figures 4A, 4B:
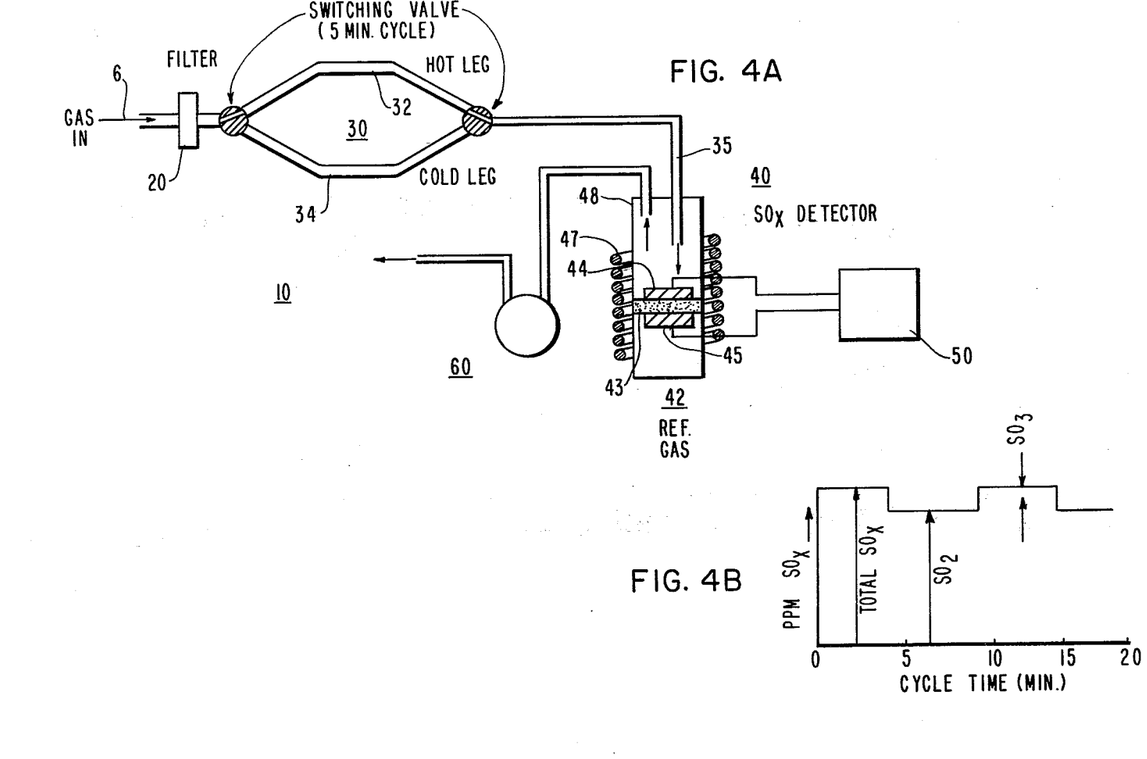
FIG. 4A is a schematic illustration of an embodiment of the invention.
FIG. 4B is a graphical illustration of the operation of the embodiment of FIG. 4A.

Although the equilibrium is a function of the water vapor content of the gas, it has been determined that for typical ambient or stack humidities, the equilibrium will be entirely in the direction of $H_2SO_4$ at temperatures below 200° C. Below this temperature $H_2SO_4$ will condense. The condensation temperature, i.e. acid dew point, is dependent on the concentrations of $H_2SO_4$ and $H_2O$ in the gas mixture. The relationship between the dew point temperature and $H_2SO_4$ concentration for several water vapor concentrations is shown in FIG. 3. It is seen that if the gas mixture is cooled to approximately 100° F., virtually all of the $H_2SO_4$ will be condensed even at water vapor concentrations typical of the ambient air (approximately 1.5 vol. %). $SO_2$ will not condense at this temperature and thus an effective means of separating $SO_2$ from $SO_3$ and $H_2SO_4$ is provided. This principle forms the basis for the use of the Goksoyr-Ross coil method for determining the $SO_3$, $H_2SO_4$ concentration in stack gases. The information illustrated in FIG. 4 can be verified in an article appearing in Chemical Engineering Progress, Vol. 71 (1974) by Verhoff and Banchero. The above-referenced Goksoyr-Ross coil method is the subject of an article appearing in the Journal of Fuel Instrumentation, Vol. 177 (1962).

It should be noted however, that the monitored gas mixture cannot be cooled below the water dew point inasmuch as condensation of water in the condenser will result in conversion of $SO_2$ to $SO_3$. The novel technique disclosed herein involves the combination of the above-disclosed technique for the controlled cooling of the sample of monitored gas and the use of a solid electrolyte $SO_x$ detector to produce a device for real time monitoring of the presence of $SO_3$, $H_2SO_4$ in a monitored stack gas. In a stack gas $SO_3$ and $H_2SO_4$ are closely associated and distinct from $SO_2$. It will be apparent from the following discussion that numerous variations of the disclosed technique can be employed to adapt the device for use with gases of widely varying $SO_3$ content.

Figures 5A, 5B:
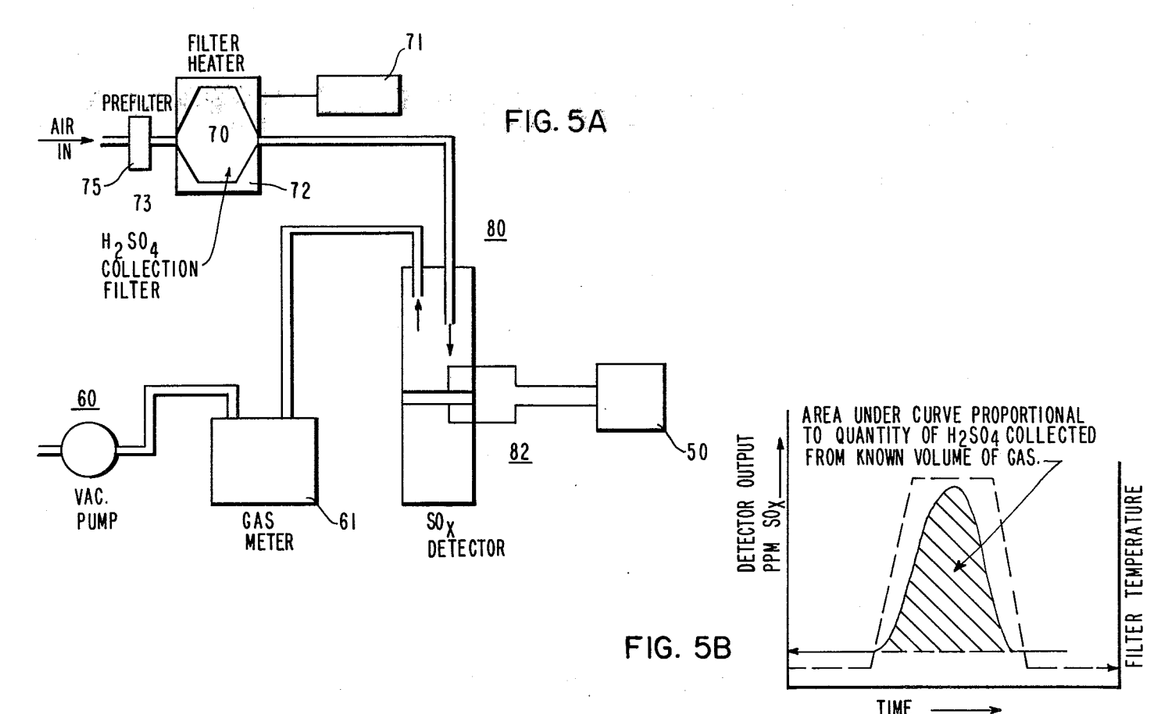
FIG. 5A is a schematic illustration of an alternate embodiment of the invention.
FIG. 5B is a graphical illustration of the operating of the embodiment of FIG. 5A.
Figure 6A:
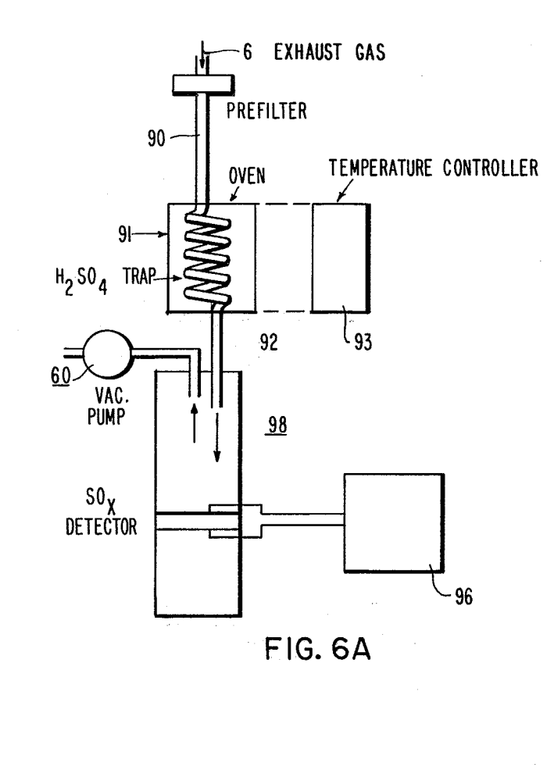
FIG. 6A is a second alternate embodiment of the invention.

The embodiments of FIGS. 4A, 5A and 6A are those of sampling systems wherein a sample of the monitoring gas, i.e. ambient air, exhaust gas, etc., is drawn into a measuring apparatus.

The embodiment of FIG. 4A illustrates an $SO_3$, $H_2SO_4$ monitoring system suitable for use in monitoring stack gases with relatively high $SO_3$ content, i.e. greater than 10 parts per million. The detector system 10 of FIG. 5A includes a heated filter 20, a hot/cold leg gas bypass apparatus 30 and an $SO_x$ detector 40. A sample of the monitored gas environment G is initially passed through a prefilter 20 heated to a temperature of about 300° C. to remove particulates from the gas sample before the gas sample reaches the detector 40. By switching the sample of monitored gas G between the hot leg 32 at a temperature of about 300° C., and the cold leg 34 at a temperature of about 40° C., of the gas bypass apparatus 30, total $SO_x$ and $SO_2$ can be separately and alternately measured by the detector 40. The difference between the measured concentration of $SO_x$ and $SO_2$ is a measurement of the $SO_3$, $H_2SO_4$ concentration in the monitored gas G. The $SO_3$ content is quantitatively condensed as $H_2SO_4$ in the cold leg 34. The operation of the system 10 on the basis of 5 minute cycle times between the sample gas flow through the hot leg 32 and the cold leg 34 is graphically illustrated in FIG. 4B. The EMF output signals sequentially generated by the detector 40 in response to the alternate supply of the monitored gas through the hot and cold legs 32 and 34 is transmitted to a conventional subtracting circuit 50. The circuit 50 subtracts the two signals and generates an output indicative of the $SO_3$, $H_2SO_4$ concentration of the monitored gas G.

The detector 40 consists of a solid electrolyte electrochemical cell 42 comprising a solid electrolyte member 43 having a sensing electrode 44 disposed on one surface and a reference electrode 45 disposed on the opposite surface. The solid electrolyte cell 42, which is constructed as described above in accordance with the teachings of the above-referenced patent, is positioned within a housing 48 so as to isolate the monitored sample gas G which contacts the sensing electrode 44 from the reference electrode 45. An $SO_x$ stable reference is provided in contact with the reference electrode such that the operation of the cell 42 in accordance with the above Nernst equation. The temperature of the detector 40 is maintained constant by the heater 47. The monitored sample gas introduced to the sensing electrode 44 via the inlet tube 35 is removed from the housing via a pump system 60.

A technique for monitoring $H_2SO_4$ in atmospheric gas where little, if any, $SO_3$ is present is illustrated in FIGS. 5A and 5B. The gas G is initially cooled by a cooler 73 to separate $H_2SO_4$ from $SO_2$. The $H_2SO_4$ is collected by a filter on trap 70. The remaining gas volume is removed by the pump 60 through a gas meter 61 which measures the volume of gas sampled. This information, in accordance with FIG. 5B, is used in determining the $SO_3$ concentration of the gas sampled during a predetermined period of time. Following a collection period of several hours or days, the filter 70 is heated through the operation of a temperature controller 71 and an over member 72 to volatilize the trapped $H_2SO_4$ and produce $H_2SO_4$. The $H_2SO_4$ is then transmitted to the $SO_x$ detector 80 consistingof the solid electrolyte electrochemical cell 82 positioned within housing 84 and an EMF signal is generated by the cell 82 which is indicative of the $H_2SO_4$ concentration collected over a period of time. Referring to the graphical illustration of FIG. 5B, the area under the $H_2SO_4$ response curve is indicative of the amount of acid collected from a known volume of ambient gas. As indicated with respect to the embodiment of FIG. 5A, a heated prefilter 75 heated to a temperature of about 150° C. or higher can be included upstream of the filter 70 to retain solid particulate matter.

Figure 6B:
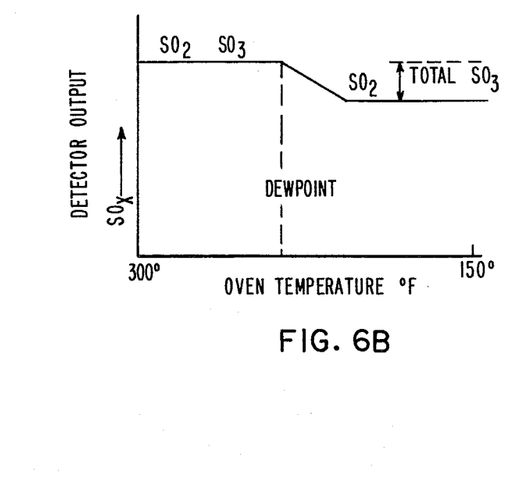
FIG. 6B is a graphical illustration of the embodiment of FIG. 6A.
Figure 7:
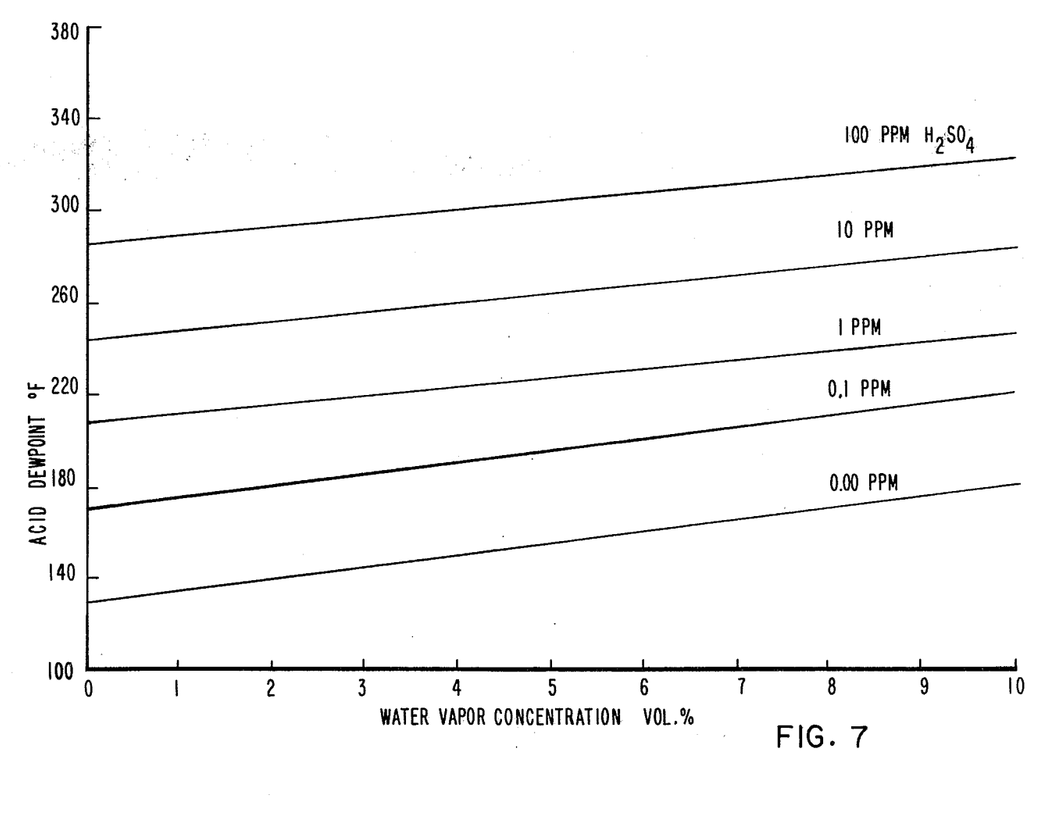
FIG. 7 is a graphical illustration of the moisture content of a gas as a function of the acid dew point and the $H_2SO_4$ concentration.

Yet another embodiment of the $SO_3$, $H_2SO_4$ detection technique is illustrated in FIGS. 6A and 6B. In this implementation the inlet tube 90 to the $SO_x$ detector 98 includes a heated prefilter 89 and a variable temperature trap 91 consisting of an oven 92 and a temperature control 93. The prefilter 89 is heated to a temperature of about 150° C. or higher. At temperatures of approximately 150° F., both $SO_2$ and $SO_3$, $H_2SO_4$ through the trap 91 and are detected by the sensor 98 to provide a total $SO_x$ indication. As the temperature of the trap 91 is lowered via the temperature controller 93, a temperature will be reached where $SO_3$ begins to be converted to $H_2SO_4$ and condensing begins in the trap 91. This temperature is the $H_2SO_4$ acid dew point. If cooling is continued, a temperature is reached where all of the $SO_3$ is converted to $H_2SO_4$ and is condensed out of the sample gas stream G entering inlet tube 90. The total change in the EMF signal generated by the detector 98 is equivalent to the $SO_3$, concentration of the sample gas G. This information regarding the acid dew point temperature and $SO_3$, $H_2SO_4$ concentration of the monitored gas G can be used to determine the moisture content of the monitored gas G in accordance with the graphical illustration of FIG. 7.

It is apparent from the above that a single apparatus can be employed to measure four important parameters of an exhaust gas, i.e. $SO_2$ concentration, $SO_3$ concentration, $H_2O$ concentration and $H_2SO_4$ acid dew point temperature.

In each of the monitoring systems described above, the choice of materials should eliminate those which would act as catalysts for the conversion of $SO_2$ to $SO_3$. While most metals promote oxidation of $SO_2$, quartz and porcelain can be considered as inert materials for use as monitored gas input lines, variable temperature coils and traps, etc. A variety of filter materials including quartz fiber, nucleopore, and Teflon have been found to be inert, efficient collectors for $H_2SO_4$ in the presence of $SO_2$.

We claim:

1. A method of monitoring $SO_3$, $H_2SO_4$ in the presence of $SO_2$ in a monitored gas environment containing $H_2O$ comprising the steps of:
    measuring the combined $SO_2$ and $SO_3$ content of a sample of the monitored gas environment;
    separating $SO_2$ from the $SO_3$, and $H_2SO_4$ by cooling the sample to a temperature which is sufficient to convert $SO_3$ in the presence of $H_2O$ to $H_2SO_4$, but which is not sufficient to condense $SO_2$;
    measuring the $SO_2$ content of the sample following said separating step; and
    determining the $SO_3$, $H_2SO_4$ content of the monitored gas environment on the basis of the difference between the measurement of the combined $SO_2$ and $SO_3$, $H_2SO_4$ and the measurement of the $SO_2$ following said separating step.

2. A method as claimed in claim 1 wherein the temperature for converting $SO_3$ in the presence of $H_2O$ to the $H_2SO_4$ by said cooling is above the water dew point.

3. A method as claimed in claim 1 wherein the temperature of said cooling is less than approximately 200° C.

4. A method as claimed in claim 1 further including the step of filtering said sample of the monitored gas prior to said cooling step to remove particulates from the gas sample.

5. A method as claimed in claim 1 further including the step of sensing the temperature at which the cooling begins to convert the $SO_3$ to $H_2SO_4$, said temperature corresponding to the $H_2SO_4$ acid dew point.

6. A method as claimed in claim 1 further including the steps of determining the temperature at which the conversion of $SO_3$ to $H_2SO_4$ begins, said temperature corresponding to the $H_2SO_4$ acid dew point, and determining the moisture content of the monitored gas environment as a function of the acid dew point and the $SO_3$ content of the monitored gas environment.

7. A method of monitoring $SO_3$, $H_2SO_4$ in the presence of $SO_2$ in a monitored gas environment containing $H_2O$ comprising the steps of:
    sampling the monitored gas environment;
    separating $SO_2$ and $SO_3$, $H_2SO_4$ by cooling the sample of the monitored gas environment to a temperature which is sufficient to convert $SO_3$ in the presence of $H_2O$ to $H_2SO_4$, but which is not sufficient to condense $SO_2$;
    trapping the resulting $H_2SO_4$ over a period of time;
    measuring the volume of monitored gas environment which is sampled during said period of time;
    heating the $H_2SO_4$ collected by said trapping step to produce $H_2SO_4$ vapor; and
    measuring the $H_2SO_4$ vapor produced by said heating step in terms of said volume of monitored gas environment to determine the $SO_3$, $H_2SO_4$ content of said monitored gas environment.

* * * * *